US008410263B2

(12) United States Patent
Madden et al.

(10) Patent No.: US 8,410,263 B2
(45) Date of Patent: Apr. 2, 2013

(54) HIGH-PURITY TEXAPHYRIN METAL COMPLEXES

(75) Inventors: Hugo Madden, Palo Alto, CA (US); Greg Hemmi, Sunnyvale, CA (US); Tarak Mody, Sunnyvale, CA (US)

(73) Assignee: Pharmacyclics, Inc., Sunnyvale, CA (US)

(*) Notice: Subject to any disclaimer, the term of this patent is extended or adjusted under 35 U.S.C. 154(b) by 496 days.

(21) Appl. No.: 12/611,896

(22) Filed: Nov. 3, 2009

(65) Prior Publication Data

US 2010/0048916 A1    Feb. 25, 2010

Related U.S. Application Data

(62) Division of application No. 11/235,475, filed on Sep. 26, 2005, now abandoned.

(51) Int. Cl.
C07D 225/06 (2006.01)
C07D 487/22 (2006.01)
C07C 43/205 (2006.01)
C07C 205/06 (2006.01)

(52) U.S. Cl. ......... 540/465; 540/472; 568/587; 568/608

(58) Field of Classification Search .......... 540/465, 540/472; 568/587, 608
See application file for complete search history.

(56) References Cited

U.S. PATENT DOCUMENTS

| | | | |
|---|---|---|---|
| 3,845,770 A | 11/1974 | Theeuwes et al. | |
| 4,326,525 A | 4/1982 | Swanson et al. | |
| 4,902,514 A | 2/1990 | Barclay et al. | |
| 4,935,498 A | 6/1990 | Sessler et al. | |
| 4,992,445 A | 2/1991 | Lawter et al. | |
| 5,001,139 A | 3/1991 | Lawter et al. | |
| 5,011,472 A | 4/1991 | Aebischer et al. | |
| 5,023,252 A | 6/1991 | Hsieh | |
| 5,041,078 A | 8/1991 | Matthews et al. | |
| 5,120,411 A | 6/1992 | Sessler et al. | |
| 5,159,065 A | 10/1992 | Sessler et al. | |
| 5,162,509 A | 11/1992 | Sessler et al. | |
| 5,252,720 A | 10/1993 | Sessler et al. | |
| 5,256,399 A | 10/1993 | Sessler et al. | |
| 5,272,142 A | 12/1993 | Sessler et al. | |
| 5,292,414 A | 3/1994 | Sessler et al. | |
| 5,302,714 A | 4/1994 | Sessler et al. | |
| 5,369,101 A | 11/1994 | Sessler et al. | |
| 5,432,171 A | 7/1995 | Sessler et al. | |
| 5,439,570 A | 8/1995 | Sessler et al. | |
| 5,451,576 A | 9/1995 | Sessler et al. | |
| 5,457,183 A | 10/1995 | Sessler et al. | |
| 5,457,195 A | 10/1995 | Sessler et al. | |
| 5,475,104 A | 12/1995 | Sessler et al. | |
| 5,504,205 A | 4/1996 | Sessler et al. | |
| 5,525,325 A | 6/1996 | Sessler et al. | |
| 5,530,122 A * | 6/1996 | Dow et al. ............. | 540/474 |
| 5,530,123 A | 6/1996 | Sessler et al. | |
| 5,543,123 A | 8/1996 | Hofmann et al. | |
| 5,559,207 A | 9/1996 | Sessler et al. | |
| 5,565,552 A | 10/1996 | Magda et al. | |
| 5,567,687 A | 10/1996 | Magda et al. | |
| 5,569,759 A | 10/1996 | Sessler et al. | |
| 5,580,543 A | 12/1996 | Sessler et al. | |
| 5,583,220 A | 12/1996 | Sessler et al. | |
| 5,587,371 A | 12/1996 | Sessler et al. | |
| 5,587,463 A | 12/1996 | Sessler et al. | |
| 5,591,422 A | 1/1997 | Hemmi et al. | |
| 5,594,136 A | 1/1997 | Sessler et al. | |
| 5,595,726 A | 1/1997 | Magda et al. | |
| 5,599,923 A | 2/1997 | Sessler et al. | |
| 5,599,928 A | 2/1997 | Hemmi et al. | |
| 5,601,802 A | 2/1997 | Hemmi et al. | |
| 5,607,924 A | 3/1997 | Magda et al. | |
| 5,616,345 A | 4/1997 | Geoghegan et al. | |
| 5,622,946 A | 4/1997 | Sessler et al. | |
| 5,672,490 A | 9/1997 | Sessler et al. | |
| 5,714,328 A | 2/1998 | Magda et al. | |
| 5,775,339 A | 7/1998 | Woodburn et al. | |
| 5,776,925 A | 7/1998 | Young et al. | |
| 5,798,491 A | 8/1998 | Magda et al. | |
| 5,801,229 A | 9/1998 | Sessler et al. | |
| 5,955,586 A | 9/1999 | Sessler et al. | |
| 5,969,111 A | 10/1999 | Sessler et al. | |
| 6,022,959 A | 2/2000 | Magda et al. | |
| 6,638,924 B2 | 10/2003 | Mody et al. | |
| 2003/0153493 A1 | 8/2003 | Fan | |
| 2005/0196466 A1 | 9/2005 | Magda | |
| 2007/0072838 A1 | 3/2007 | Madden et al. | |

FOREIGN PATENT DOCUMENTS

| | | |
|---|---|---|
| WO | WO-90-10633 | 9/1990 |
| WO | WO-94-09003 | 4/1994 |
| WO | WO-94-29316 | 12/1994 |
| WO | WO-95-10307 | 4/1995 |
| WO | WO-95-21845 | 8/1995 |
| WO | WO-96-09315 | 3/1996 |
| WO | WO-96-38461 | 12/1996 |

(Continued)

OTHER PUBLICATIONS

March, J., Advanced Organic Chemistry, 1993, John Wiley & Sons, Inc., 4th ed, p. 357-362.*
Sessler et al., "Texaphyrins-New Drugs with diverse clinical Applications in Radiation and Photodynamic Therapy," Biochem Pharm. 59:733-739 (2000).
EP 05807302 Supplementary Search Report dated May 25, 2010.
Sessler et al., "One-Electron Reduction and Oxidation Studies of the Radiation Sensitizer Gadolinium (III) Texaphyrin (PCI-0120) and Other Water Soluble Metallotexaphyrins," Journal of Physical Chemistry A (1999), pp. 787-794, vol. 103, No. 7, American Chemical Society, published on Web Feb. 3, 1999.

(Continued)

*Primary Examiner* — Shaojia Anna Jiang
*Assistant Examiner* — Jonathan S Lau
(74) *Attorney, Agent, or Firm* — Wilson, Sonsini, Goodrich & Rosati (57) ABSTRACT

Disclosed herein are the methods and compositions for the improved synthesis of texaphyrin metal complexes. The improved synthesis results in high-purity compositions of texaphyrin metal complexes in which more than about 98% of the texaphyrin metal complexes in the composition have the same structure and/or the same molecular weight. Further described herein are pharmaceutical compositions comprising such high-purity compositions, and the use of such high-purity compositions in the treatment of cancer and cardiovascular diseases and disorders.

4 Claims, 3 Drawing Sheets

FOREIGN PATENT DOCUMENTS

| WO | WO-96-40253 | 12/1996 |
| WO | WO-97-26915 | 7/1997 |
| WO | WO-97-35617 | 10/1997 |
| WO | WO-97-46262 | 12/1997 |
| WO | WO-98-07733 | 2/1998 |
| WO | WO 99/06411 | 2/1999 |
| WO | WO-00-01413 | 1/2000 |
| WO | WO-00-09522 | 2/2000 |
| WO | WO-02-17908 | 3/2002 |
| WO | WO-02-17910 A1 | 3/2002 |
| WO | WO-2004-050716 A2 | 6/2004 |

OTHER PUBLICATIONS

Garini et al., *Special Bioimaging*, John Wiley & Sons, NY, NY (1996) pp. 87-124.

Mehta et al., "Lead-In Phase to Randomized Trial of Metoxafin Gadolinium and Whole-Brain Radiation for Patients with Brain Metastases: Centralized Assessment of Magnetic Resonance Imaging, Neocognitive, and Neurologic End Points," J. of Clin. Onc., vol. 20, No. 16 (Aug. 15, 2002), pp. 3445-3453.

Rockwell et al., "Growth and Cell Population Kinetics of Single and Multiple KHT Sarcomas," Cell Tissue Kinetics, vol. 1, 1972, pp. 449-457.

PCT/US05/34684 Search Report dated Jul. 26, 2006.

Sessler et al., "Synthesis and Structural Characterization of Lanthanide(III) Texaphyrins," Inorganic Chem. 32:3175-3187 (1993).

Gennaro, A.R. "Quality Assurance and Control," from Remington: The Science and Practice of Pharmacy, 2000, Lippincott Williams & Wilkins, $20^{th}$ ed., pp. 980-983.

Young et al., "Gadolinium (III) texaphyrin: A tumor selective radiation sensitizer that is detectable by MRI," PNAS USA 93:6610-6615 (1996).

Zhao et al., "Strategies and Methods for Purifying Organic Compounds and Combinatorial Libraries," Analysis and Purification Methods in Combinatorial Chemistry, Yan, B. ed., 2004, John WIley & Sons, Inc., vol. 163, pp. 255-280.

\* cited by examiner

HIGH-PURITY TEXAPHYRIN METAL COMPLEXES

This application is a divisional patent application of U.S. application Ser. No. 11/235,475, filed Sep. 26, 2005 entitled "HIGH-PURITY TEXAPHYRIN METAL COMPLEXES", which is herein incorporated by reference.

FIELD OF THE INVENTION

Disclosed herein are high-purity texaphyrin metal complexes, methods for making such complexes, and the use of such high-purity texaphyrin metal complexes to treat diseases, disorders and conditions, including cancer and atherosclerosis.

BACKGROUND OF THE INVENTION

Cancer is a serious threat to modern society. Worldwide, more than 10 million people are diagnosed with cancer every year and it is estimated that this number will grow to 15 million new cases every year by 2020. Cancer causes six million deaths every year or 12% of the deaths worldwide. Current treatment options are often limited but widely employed. Of the 1.2 million patients newly diagnosed with cancer in the United States annually, approximately 50% will be treated with radiation therapy as part of initial disease management. Approximately 150,000 additional patients with recurrent cancer may receive radiation therapy each year in the U.S. Chemotherapy is administered to about 350,000 cancer patients in the U.S. annually.

High levels of circulating cholesterol are associated with atherosclerosis, which may result in life-threatening blockages of blood vessels to the heart and brain. Unstable angina, myocardial infarction (heart attack) and sudden ischemic death remain the leading cause of morbidity and mortality in developed nations. Current estimates indicate that 1.1 million people in the U.S. annually will have a new or recurrent coronary attack, and over 45 percent of these patients may die from the coronary attack.

Texaphyrins are small molecules having a ring-shaped chemical structure containing one of several metal atoms. The physical and chemical characteristics of texaphyrin molecules are determined by the properties of the ring and the type of metal atom inserted into the ring. Texaphyrins are designed to selectively concentrate in diseased tissue such as tumor cells and atherosclerotic plaque inside blood vessels. Inside diseased cells, texaphyrins block crucial steps in cellular metabolism and disrupt bioenergetic processes. Texaphyrins are designed to provide a valuable therapeutic approach to a broad range of diseases. These can be used for the treatment of a variety of diseases, including cancer, atherosclerosis and cardiovascular diseases, and potentially neurodegenerative diseases, inflammatory diseases, and HIV/AIDS.

SUMMARY OF THE INVENTION

Disclosed herein are compositions comprising high-purity texaphyrin metal complexes, wherein the identity of the substituents on the texaphyrin complex are at least about 98% identical on all texaphyrin complexes in a sample. Also disclosed herein are compositions comprising high-purity synthetic precursors to high-purity texaphyrin complexes. Also disclosed herein are methods for synthesizing such high-purity texaphyrin metal complexes and such high-purity precursors. Also disclosed herein are methods for pegylating an aromatic moiety, wherein the identity of the poly(ethylene glycol) substituents on the aromatic moiety are at least about 98% identical on all aromatic moieties in a sample. Also disclosed herein are pharmaceutical compositions comprising such high-purity texaphyrin metal complexes. Also disclosed herein are methods for treating a disorder, disease or condition in a human patient comprising administering to the patient an effective amount of such high-purity texaphyrin metal complexes.

A first aspect disclosed herein are high-purity compositions comprising a compound of Formula 1 wherein: M is a trivalent metal cation selected from the group consisting of $Gd^{+3}$, and $Lu^{+3}$; each X is independently selected from the group consisting of $OH^-$, $AcO^-$, $Cl^-$, $Br^-$, $I^-$, $F^-$, $H_2PO_4^-$, $ClO^-$, $ClO_2^-$, $ClO_3^-$, $ClO_4^-$, $HCO_3^-$, $HSO_4^-$, $NO_3^-$, $N_3^-$, $CN^-$, $SCN^-$, and $OCN^-$; $R_3$, $R_4$, $R_5$, $R_6$, $R_7$ and $R_8$ are independently H, OH, $C_nH_{(2n+1)}O_y$, or $OC_nH_{(2n+1)}O_y$, and $R_1$, $R_2$ are independently H or $C_1$-$C_6$ alkyl where at least one of $R_3$, $R_4$, $R_5$, $R_6$, $R_7$ and $R_8$ is $OC_nH_{(2n+1)}O_y$ or $OC_nH_{(2n+1)}O_y$, having at least one hydroxyl substituent; n is a positive integer from 1 to 11; y is zero or a positive integer less than or equal to n; each x is independently selected from the group consisting of 2, 3, 4, 5, and 6; wherein at least about 98.4% of compounds of Formula 1 in the composition have the same structure. In one embodiment, M is $Gd^{+3}$. In one embodiment, $R_4$ and $R_7$ are $C_3H_6OH$; $R_5$ and $R_6$ are $C_2H_5$; $R_3$ and $R_8$ are $CH_3$; $R_1$ and $R_2$ are H. In one embodiment, each x is 3. In one embodiment, each X is $AcO^-$. In another embodiment, M is $Lu^{+3}$. In one embodiment, $R_4$ and $R_7$ are $C_3H_6OH$; $R_5$ and $R_6$ are $C_2H_5$; $R_3$ and $R_8$ are $CH_3$; $R_1$ and $R_2$ are H. In one embodiment, each x is 3. In one embodiment, each X is $AcO^-$. In a further or alternate embodiment, each X is selected from the group consisting of sugar derivatives, cholesterol derivatives, PEG acids, organic acids, organosulfates, organophosphates, phosphates or inorganic ligands. In a further or alternate embodiment, X is derived from an acid selected from the group consisting of gluconic acid, glucoronic acid, cholic acid, deoxycholic acid, methylphosphonic acid, phenylphosphonic acid, phosphoric acid, formic acid, propionic acid, butyric acid, pentanoic acid, 3,6,9-trioxodecanoic acid, 3,6-dioxoheptanoic acid, 2,5-dioxoheptanoic acid, methylvaleric acid, glycolic acid, pyruvic acid, oxalic acid, malic acid, malonic acid, succinic acid, maleic acid, fumaric acid, tartaric acid, citric acid, methanesulfonic acid, ethanesulfonic acid, benzoic acid, salicylic acid, 3-fluorobenzoic acid, 4-aminobenzoic acid, cinnamic acid, mandelic acid, and p-toluenesulfonic acid.

In one embodiment, at least about 98.4% of compounds of Formula 1 in the composition have the same molecular weight, wherein the same molecular weight excludes isotopic variations. In one embodiment, at least about 98.7% of compounds of Formula 1 in the composition have the same molecular weight, wherein the same molecular weight excludes isotopic variations. In one embodiment, at least about 99% of compounds of Formula 1 in the composition have the same molecular weight, wherein the same molecular weight excludes isotopic variations. In one embodiment, at least about 99.3% of compounds of Formula 1 in the composition have the same molecular weight, wherein the same molecular weight excludes isotopic variations. In one embodiment, at least about 99.5% of compounds of Formula 1 in the composition have the same molecular weight, wherein the same molecular weight excludes isotopic variations. In one embodiment, at least about 98.7% of compounds of Formula 1 in the composition have the same structure. In one embodiment, at least about 99% of compounds of Formula 1 in the composition have the same structure. In one embodiment, at least about 99.3% of compounds of Formula 1 in the composition have the same structure. In one embodiment, at least about 99.5% of compounds of Formula 1 in the composition have the same structure.

A second aspect disclosed herein are high-purity compositions comprising a compound of Formula 2:

2 wherein: $R_3$, $R_4$, $R_5$, $R_6$, $R_7$ and $R_8$ are independently H, OH, $C_nH_{(2n+1)}O_y$, or and $R_1$, $R_2$ are independently H or $C_1$-$C_6$ alkyl where at least one of $R_3$, $R_4$, $R_5$, $R_6$, $R_7$ and $R_8$ is $C_nH_{(2n+1)}O_y$ or $OC_nH_{(2n+1)}O_y$, having at least one hydroxyl substituent; n is a positive integer from 1 to 11; y is zero or a positive integer less than or equal to n; each x is independently selected from the group consisting of 2, 3, 4, 5, and 6; and acceptable acid addition salts thereof; wherein at least about 98.4% of compounds of Formula 2 in the composition have the same structure. In one embodiment, $R_4$ and $R_7$ are $C_3H_6OH$; $R_5$ and $R_6$ are $C_2H_5$; $R_3$ and $R_8$ are $CH_3$; $R_1$ and $R_2$ are H. In one embodiment, each x is 3. In one embodiment, the acceptable acid addition salt is selected from the group consisting of hydrochloric acid, hydrobromic acid, sulfuric acid, nitric acid, phosphoric acid, methanesulfonic acid, ethanesulfonic acid, p-toluenesulfonic acid, and salicylic acid. In one embodiment, the acceptable acid addition salt is a hydrochloride salt.

In one embodiment, at least about 98.4% of compounds of Formula 2 in the composition have the same molecular weight, wherein the same molecular weight excludes isotopic variations. In one embodiment, at least about 98.7% of compounds of Formula 2 in the composition have the same molecular weight, wherein the same molecular weight excludes isotopic variations. In one embodiment, at least about 99% of compounds of Formula 2 in the composition have the same molecular weight, wherein the same molecular weight excludes isotopic variations. In one embodiment, at least about 99.3% of compounds of Formula 2 in the composition have the same molecular weight, wherein the same molecular weight excludes isotopic variations. In one embodiment, at least about 99.5% of compounds of Formula 2 in the composition have the same molecular weight, wherein the same molecular weight excludes isotopic variations. In one embodiment, at least about 98.7% of compounds of Formula 2 in the composition have the same structure. In one embodiment, at least about 99% of compounds of Formula 2 in the composition have the same structure. In one embodiment, at least about 99.3% of compounds of Formula 2 in the composition have the same structure. In one embodiment, at least about 99.5% of compounds of Formula 2 in the composition have the same structure.

A third aspect disclosed herein are high-purity compositions comprising a compound of Formula 4

4 wherein $R_1$ and $R_2$ are independently H or $C_1$-$C_6$ alkyl; each x is independently selected from the group consisting of 2, 3, 4, 5, and 6; and wherein at least about 98.4% of compounds of Formula 4 in the composition have the same structure. In one embodiment, $R_1$ and $R_2$ are H. In one embodiment, each x is 3.

In one embodiment, at least about 98.4% of compounds of Formula 4 in the composition have the same molecular weight, wherein the same molecular weight excludes isotopic variations. In one embodiment, at least about 98.7% of compounds of Formula 4 in the composition have the same molecular weight, wherein the same molecular weight excludes isotopic variations. In one embodiment, at least about 99% of compounds of Formula 4 in the composition have the same molecular weight, wherein the same molecular weight excludes isotopic variations. In one embodiment, at least about 99.3% of compounds of Formula 4 in the composition have the same molecular weight, wherein the same molecular weight excludes isotopic variations. In one embodiment, at least about 99.5% of compounds of Formula 4 in the composition have the same molecular weight, wherein the same molecular weight excludes isotopic variations. In one embodiment, at least about 98.7% of compounds of Formula 4 in the composition have the same structure. In one embodiment, at least about 99% of compounds of Formula 4 in the composition have the same structure. In one embodiment, at least about 99.3% of compounds of Formula 4 in the composition have the same structure. In one embodiment, at least about 99.5% of compounds of Formula 4 in the composition have the same structure.

A fourth aspect disclosed herein are high-purity compositions comprising a compound of Formula 5

5 wherein $R_1$ and $R_2$ are independently H or $C_1$-$C_6$ alkyl; each x is independently selected from the group consisting of 2, 3, 4, 5, and 6; and wherein at least about 98.4% of compounds of Formula 5 in the composition have the same structure. In one embodiment, $R_1$ and $R_2$ are H. In one embodiment, each x is 3.

In one embodiment, at least about 98.4% of compounds of Formula 5 in the composition have the same molecular weight, wherein the same molecular weight excludes isotopic variations. In one embodiment, at least about 98.7% of compounds of Formula 5 in the composition have the same molecular weight, wherein the same molecular weight excludes isotopic variations. In one embodiment, at least about 99% of compounds of Formula 5 in the composition have the same molecular weight, wherein the same molecular weight excludes isotopic variations. In one embodiment, at least about 99.3% of compounds of Formula 5 in the composition have the same molecular weight, wherein the same molecular weight excludes isotopic variations. In one embodiment, at least about 99.5% of compounds of Formula 5 in the composition have the same molecular weight, wherein the same molecular weight excludes isotopic variations. In one embodiment, at least about 98.7% of compounds of Formula 5 in the composition have the same structure. In one embodiment, at least about 99% of compounds of Formula 5 in the composition have the same structure. In one embodiment, at least about 99.3% of compounds of Formula 5 in the composition have the same structure. In one embodiment, at least about 99.5% of compounds of Formula 5 in the composition have the same structure.

A fifth aspect disclosed herein are methods for synthesizing a purified sample of a compound of Formula 4

4 wherein $R_1$ and $R_2$ are independently H or $C_1$-$C_6$ alkyl; each x is independently selected from the group consisting of 2, 3, 4, 5, and 6; and wherein at least about 98.4% of the compounds of Formula 4 in the purified sample have the same structure comprising: reacting a compound of Formula 5

5 with about 90% $HNO_3$ in AcOH at about 0-5° C. for at least 30 minutes, wherein at least about 98.4% of the compounds of Formula 4 formed in the purified sample have the same structure. In one embodiment, $R_1$ and $R_2$ are H. In one embodiment, each x is 3.

In one embodiment, at least about 98.4% of compounds of Formula 4 in the purified sample have the same molecular weight, wherein the same molecular weight excludes isotopic variations. In one embodiment, at least about 98.7% of compounds of Formula 4 in the purified sample have the same molecular weight, wherein the same molecular weight excludes isotopic variations. In one embodiment, at least about 99% of compounds of Formula 4 in the purified sample have the same molecular weight, wherein the same molecular weight excludes isotopic variations. In one embodiment, at least about 99.3% of compounds of Formula 4 in the purified sample have the same molecular weight, wherein the same molecular weight excludes isotopic variations. In one embodiment, at least about 99.5% of compounds of Formula 4 in the purified sample have the same molecular weight, wherein the same molecular weight excludes isotopic variations. In one embodiment, at least about 98.7% of compounds of Formula 4 in the purified sample have the same structure. In one embodiment, at least about 99% of compounds of Formula 4 in the purified sample have the same structure. In one embodiment, at least about 99.3% of compounds of Formula 4 in the purified sample have the same structure. In one embodiment, at least about 99.5% of compounds of Formula 4 in the purified sample have the same structure.

A sixth aspect disclosed are methods for synthesizing a purified sample of a compound of Formula 5

5 wherein $R_1$ and $R_2$ are independently H or $C_1$-$C_6$ alkyl; each x is independently selected from the group consisting of 2, 3, 4, 5, and 6; and wherein at least about 98.4% of the compounds of Formula 5 in the purified sample have the same structure comprising: reacting tosylated compound of Formula 7

7 with o-dihydroxybenzene of Formula 6 in the presence of $K_2CO_3$ and an aprotic solvent and heating the mixture at about 65° C. for about 24 hr wherein at least about 98.4% of the compound of Formula 5 formed in the purified sample have the same structure. In a further or alternative embodiment, the mixture is heated at the reflux temperature of the aprotic solvent.

In one embodiment, aprotic solvent is selected from the group consisting of aldehydes, ketones, dimethyl sulfoxide, dimethyl formamide, pyridine, diethyl ether, ethyl acetate, propyl acetate, isopropyl acetate, butyl acetate, acetonitrile, benzonitrile, sulfur dioxide, tetrahydrofuran, and hexamethyl phophoramide. In one embodiment, the aprotic solvent is tetrahydrofuran. In a further or alternative embodiment, $R_1$ and $R_2$ are H. In one embodiment, each x is 3, and further, the aprotic solvent is tetrahydrofuran.

In one embodiment, at least about 98.4% of compounds of Formula 5 in the purified sample have the same molecular weight, wherein the same molecular weight excludes isotopic variations. In one embodiment, at least about 98.7% of compounds of Formula 5 in the purified sample have the same molecular weight, wherein the same molecular weight excludes isotopic variations. In one embodiment, at least about 99% of compounds of Formula 5 in the purified sample have the same molecular weight, wherein the same molecular weight excludes isotopic variations. In one embodiment, at least about 99.3% of compounds of Formula 5 in the purified sample have the same molecular weight, wherein the same molecular weight excludes isotopic variations. In one embodiment, at least about 99.5% of compounds of Formula 5 in the purified sample have the same molecular weight, wherein the same molecular weight excludes isotopic variations. In one embodiment, at least about 98.7% of compounds of Formula 5 in the purified sample have the same structure. In one embodiment, at least about 99% of compounds of Formula 5 in the purified sample have the same structure. In one embodiment, at least about 99.3% of compounds of Formula 5 in the purified sample have the same structure. In one embodiment, at least about 99.5% of compounds of Formula 5 in the purified sample have the same structure.

A seventh aspect disclosed herein are pharmaceutical compositions comprising a compound according to Formula 1 and a pharmaceutically acceptable carrier, wherein at least about 98.4% of the compounds of Formula 1 in the pharmaceutical composition have the same structure. In one embodiment, M is $Gd^{+3}$. In one embodiment, $R_4$ and $R_7$ are $C_3H_6OH$; $R_5$ and $R_6$ are $C_2H_5$; $R_3$ and $R_8$ are $CH_3$; $R_1$ and $R_2$ are H. In one embodiment, each x is 3. In one embodiment, each X is $AcO^-$. In another embodiment, M is $Lu^{+3}$. In a further embodiment, $R_4$ and $R_7$ are $C_3H_6OH$; $R_5$ and $R_6$ are $C_2H_5$; $R_3$ and $R_8$ are $CH_3$; $R_1$ and $R_2$ are H. In a further embodiment, each x is 3. In a further embodiment, each X is $AcO^-$. In a further or alternate embodiment, each X is selected from the group consisting of sugar derivatives, cholesterol derivatives, PEG acids, organic acids, organosulfates, organophosphates, phosphates or inorganic ligands. In a further or alternate embodiment, X is derived from an acid selected from the group consisting of gluconic acid, glucoronic acid, cholic acid, deoxycholic acid, methylphosphonic acid, phenylphosphonic acid, phosphoric acid, formic acid, propionic acid, butyric acid, pentanoic acid, 3,6,9-trioxodecanoic acid, 3,6-dioxoheptanoic acid, 2,5-dioxoheptanoic acid, methylvaleric acid, glycolic acid, pyruvic acid, oxalic acid, malic acid, malonic acid, succinic acid, maleic acid, fumaric acid, tartaric acid, citric acid, methanesulfonic acid, ethanesulfonic acid, benzoic acid, salicylic acid, 3-fluorobenzoic acid, 4-aminobenzoic acid, cinnamic acid, mandelic acid, and p-toluenesulfonic acid.

In one embodiment, at least about 98.4% of compounds of Formula 1 in the pharmaceutical composition have the same molecular weight, wherein the same molecular weight excludes isotopic variations. In one embodiment, at least about 98.7% of compounds of Formula 1 in the pharmaceutical composition have the same molecular weight, wherein the same molecular weight excludes isotopic variations. In one embodiment, at least about 99% of compounds of Formula 1 in the pharmaceutical composition have the same molecular weight, wherein the same molecular weight excludes isotopic variations. In one embodiment, at least about 99.3% of compounds of Formula 1 in the pharmaceutical composition have the same molecular weight, wherein the same molecular weight excludes isotopic variations. In one embodiment, at least about 99.5% of compounds of Formula 1 in the pharmaceutical composition have the same molecular weight, wherein the same molecular weight excludes isotopic variations. In one embodiment, at least about 98.7% of compounds of Formula 1 in the pharmaceutical composition have the same structure. In one embodiment, at least about 99% of compounds of Formula 1 in the pharmaceutical composition have the same structure. In one embodiment, at least about 99.3% of compounds of Formula 1 in the pharmaceutical composition have the same structure. In one embodiment, at least about 99.5% of compounds of Formula 1 in the pharmaceutical composition have the same structure. In one embodiment, the pharmaceutically acceptable carrier is suitable for parenteral administration.

An eighth aspect disclosed herein, involves a method of treating a cancer by administering to a subject in need thereof an effective amount of a purified composition comprising a compound of Formula 1 wherein at least about 98.4% of the compounds of Formula 1 in the purified composition have the same structure, or a pharmaceutically acceptable salt, solvate, isomers, tautomers, metabolites, analogs, or prodrugs thereof. In one embodiment, the method further comprises of surgery, radiation therapy, chemotherapy, gene therapy, immunotherapy, or a combination thereof. In one embodiment, the cancer is selected from the group consisting of glioblastoma, lymphomas, leukemia, renal cell cancer, head and neck cancer, breast cancer, prostrate cancer, ovarian cancer, and lung cancer.

A ninth aspect disclosed herein, involves a method of treating a cardiovascular disease by administering to a subject in need thereof an effective amount of a purified composition comprising a compound of Formula 1 wherein at least about 98.4% of the compounds of Formula 1 in the purified composition have the same structure,
or a pharmaceutically acceptable salt, solvate, isomers, tautomers, metabolites, analogs, or prodrugs thereof. In one embodiment, the cardiovascular disease is selected from the group consisting of coronary artery disease, saphenous vein graft disease, and peripheral artery disease. In a further embodiment, M is $Lu^{+3}$ and the subject is further provided photodynamic therapy. In one embodiment, the photodynamic therapy is provided after the subject has been administered the compound of Formula 1. In another embodiment, the target area is illuminated with light having wavelengths between about 725 and 760 nm. In a further or alternate embodiment, each X is selected from the group consisting of sugar derivatives, cholesterol derivatives, PEG acids, organic acids, organosulfates, organophosphates, phosphates or inorganic ligands. In a further or alternate embodiment, X is derived from an acid selected from the group consisting of gluconic acid, glucoronic acid, cholic acid, deoxycholic acid, methylphosphonic acid, phenylphosphonic acid, phosphoric acid, formic acid, propionic acid, butyric acid, pentanoic acid, 3,6,9-trioxodecanoic acid, 3,6-dioxoheptanoic acid, 2,5-dioxoheptanoic acid, methylvaleric acid, glycolic acid, pyruvic acid, oxalic acid, malic acid, malonic acid, succinic acid, maleic acid, fumaric acid, tartaric acid, citric acid, methanesulfonic acid, ethanesulfonic acid, benzoic acid, salicylic acid, 3-fluorobenzoic acid, 4-aminobenzoic acid, cinnamic acid, mandelic acid, and p-toluene-sulfonic acid.

In one embodiment of the aforementioned eighth and ninth aspects, M is $Gd^{+3}$. In one embodiment, $R_4$ and $R_7$ are $C_3H_6OH$; $R_5$ and $R_6$ are $C_2H_5$; $R_3$ and $R_8$ are $CH_3$; $R_1$ and $R_2$ are H. In one embodiment, each x is 3. In one embodiment, each X is $AcO^-$. In another embodiment, M is $Lu^{+3}$. In a further embodiment, $R^4$ and $R_7$ are $C_3H_6OH$; $R_5$ and $R_6$ are $C_2H_5$; $R_3$ and $R_8$ are $CH_3$; $R_1$ and $R_2$ are H. In a further embodiment, each x is 3. In a further embodiment, each X is $AcO^-$. In a further or alternate embodiment, each X is selected from the group consisting of sugar derivatives, cholesterol derivatives, PEG acids, organic acids, organosulfates, organophosphates, phosphates or inorganic ligands. In a further or alternate embodiment, X is derived from an acid selected from the group consisting of gluconic acid, glucoronic acid, cholic acid, deoxycholic acid, methylphosphonic acid, phenylphosphonic acid, phosphoric acid, formic acid, propionic acid, butyric acid, pentanoic acid, 3,6,9-trioxodecanoic acid, 3,6-dioxoheptanoic acid, 2,5-dioxoheptanoic acid, methylvaleric acid, glycolic acid, pyruvic acid, oxalic acid, malic acid, malonic acid, succinic acid, maleic acid, fumaric acid, tartaric acid, citric acid, methanesulfonic acid, ethanesulfonic acid, benzoic acid, salicylic acid, 3-fluorobenzoic acid, 4-aminobenzoic acid, cinnamic acid, mandelic acid, and p-toluene-sulfonic acid.

In one embodiment of the aforementioned eighth and ninth aspects, at least about 98.4% of compounds of Formula 1 in the composition have the same molecular weight, wherein the same molecular weight excludes isotopic variations. In one embodiment, at least about 98.7% of compounds of Formula 1 in the composition have the same molecular weight, wherein the same molecular weight excludes isotopic variations. In one embodiment, at least about 99% of compounds of Formula 1 in the composition have the same molecular weight, wherein the same molecular weight excludes isotopic variations. In one embodiment, at least about 99.3% of compounds of Formula 1 in the composition have the same molecular weight, wherein the same molecular weight excludes isotopic variations. In one embodiment, at least about 99.5% of compounds of Formula 1 in the composition have the same molecular weight, wherein the same molecular weight excludes isotopic variations. In one embodiment, at least about 98.7% of compounds of Formula 1 in the composition have the same structure. In one embodiment, at least about 99% of compounds of Formula 1 in the composition have the same structure. In one embodiment, at least about 99.3% of compounds of Formula 1 in the composition have the same structure. In one embodiment, at least about 99.5% of compounds of Formula 1 in the composition have the same structure.

The term "chemotherapy" as described herein, refers to the administration of one or more anti-cancer drugs and/or other agents to a cancer patient by various methods, including intravenous, oral, intramuscular, intraperitoneal, intravesical, subcutaneous, transdermal, buccal, or inhalation or in the form of a suppository.

The term "old process" as described herein, refers to process described in Sessler et al in U.S. Pat. No. 5,994,535, incorporated herein by reference in its entirety.

The term "purified sample" or "purified composition" refers to a composition having a high degree of uniformity in the chemical structure (or molecular weight, excluding isotopic variations) of compounds having a particular generic chemical formula. That is, multiple compounds in a composition may be species of a particular generic chemical formula; however in a purified sample or purified composition, a high proportion of such compounds have the same chemical formula (or molecular weight, excluding isotopic variations). The value for the terms "high degree" or "high proportion" are provided specific values herein, for example, at least about 98.4%, at least about 98.7%, and the like. A purified sample or purified composition can include other chemical entities, including solvents, salts, reagents, pharmaceutical excipients, additional therapeutic agents, and the like. The defining aspect is that the composition has a high degree of uniformity in the chemical structure (or molecular weight, excluding isotopic variations) of compounds having a particular generic chemical formula (or molecular weight, excluding isotopic variations), and in particular compounds having the structure of Formula 1, Formula 2, Formula 4 and Formula 5. The uniformity of a particular purified composition or purified sample can be determined by a variety of analytical methods, including by way of example only, chromatography, and spectroscopic or spectrometric methods.

The term "parenteral administration" as described herein, refers to administration of at least one agent by means other than through the alimentary tract. Parenteral routes of administration involve injections into various compartments of the body such as but not limited to, intravenous, subcutaneous, intramuscular, intraperitoneal and the like.

The terms "pharmaceutically effective amount" or "effective amount" as described herein, refers to a nontoxic but sufficient amount of the agent to provide the desired biological, therapeutic, and/or prophylactic result. The desired results include reduction and/or alleviation of the signs, symptoms, or causes of a disease, or any other desired alteration of a biological system. An effective amount in any individual case may be determined by one of ordinary skill in the art using routine experimentation.

The term "pharmaceutically acceptable" or "pharmacologically acceptable" as described herein, may mean a material which is not biologically or otherwise undesirable, i.e., the material may be administered to an individual without causing any undesirable biological effects or interacting in a deleterious manner with any of the components of the composition in which it is contained.

The term "photodynamic therapy" as described herein, refers to a treatment that combines a light source and a photosensitizing agent (a drug that is activated by light).

The term "radiation therapy" as described herein, refers to exposing a patient to high-energy radiation, including without limitation x-rays, gamma rays, and neutrons. This type of therapy includes without limitation external-beam therapy, internal radiation therapy, implant radiation, brachytherapy, systemic radiation therapy, and radiotherapy.

The term "same molecular weight," as used herein, refers to compounds that have the same molecular weight, excluding isotopic variations and the identity of the counterions. That is, the molecular weight of a compound is determined by adding up the atomic weight of all atoms in the formula, excluding however, the counterions (i.e., the X groups in Formula 1). In particular, a compound does not have a different molecular weight from another compound, for purposes of this definition because it has a 2H instead of a 1H in a structure (i.e., isotopic variations do not constitute different molecular weights). By way of example only, compounds having the same molecular weight in reference to Formula 1 have the same M, R3, R4, R5, R6, R7, R8, R1, and R2 groups, and the same values for n, y, and x; however, the identity of the X group or groups can be different.

The term "same structure," as used herein, refers to compounds having identical chemical structures, excluding isotopic variations and counterions. By way of example only, compounds having the same structure in reference to Formula 1 have the same M, R3, R4, R5, R6, R7, R8, R1, and R2 groups, and the same values for n, y, and x; however, the identity of the X group or groups can be different.

The term "surgery" as described herein, refers to any therapeutic or diagnostic procedure that involves methodical action of the hand or of the hand with an instrument, on the body of a human or other mammal, to produce a curative, remedial, or diagnostic effect.

The term "treating" and its grammatical equivalents as described herein, refers to achieving, or attempting to achieve, a therapeutic benefit and/or a prophylactic benefit. By therapeutic benefit is meant eradication or amelioration, at least in part, of the underlying disorder being treated. For example, in a cancer patient, therapeutic benefit includes eradication or amelioration, at least in part, of the underlying cancer. Also, a therapeutic benefit includes the eradication or amelioration, at least in part, of one or more of the physiological symptoms associated with the underlying disorder such that an improvement is observed in the patient, notwithstanding the fact that the patient may still be afflicted with the underlying disorder. For prophylactic benefit, a method disclosed herein may be performed on, or a composition disclosed herein administered to, a patient at risk of developing cancer, or to a patient reporting one or more of the physiological symptoms of such conditions, even in the absence of a diagnosis of the condition.

INCORPORATION BY REFERENCE

Unless stated otherwise, all publications and patent applications mentioned in this specification are herein incorporated by reference to the same extent as if each individual publication or patent application was specifically and individually indicated to be incorporated by reference.

DETAILED DESCRIPTION OF THE INVENTION

Texaphyrins

Sessler et al reported in U.S. Pat. No. 5,994,535, incorporated herein by reference in its entirety, the synthesis of "texaphyrins", which absorb strongly in the tissue-transparent 730-770 nm range. This compound is capable of existing in both its free-base form and of supporting the formation of complexes with a variety of metal cations, such as $Cd^{2+}$, $Hg^{2+}$, $In^{3+}$, $Y^{3+}$, $Nd^{3+}$, $Eu^{3+}$, $Sm^{3+}$, $La^{3+}$, $Lu^{3+}$, $Gd^{3+}$, and other cations of the lanthanide series. Texaphyrins find use in the treatment of cancer and atherosclerosis.

Compositions of texaphyrins synthesized by the old process were polydisperse at the polyethylene glycol chain length, that is, compositions of texaphyrins synthesized by the old process comprised multiple species that differed in structure, although sharing a common generic chemical structure. This variety in structure arose, at least in part, from non-uniformity in the identity of the polyethylene glycol substituents. As a result, high purity samples (i.e., having less than about 1.6% polydispersity at the polyethylene glycol chain) were not available for therapeutic use. The synthetic processes disclosed herein, provides a breakthrough in this area by providing a method for the synthesis of high purity texaphyrins (i.e., having less than about 1.6% polydispersity at the polyethylene glycol chain).

There are a number of disadvantages associated with low purity in a sample, including, by way of example only, difficulties in solubility optimization in pharmaceutical formulations such that the effective concentrations of an agent may vary from preparation to preparation; difficulties in optimizing drug dosage; and difficulties in stabilizing formulations. The improvement in the purities of the compounds disclosed herein overcome such disadvantages of solubility, dose optimization, and drug stabilization. The improvement in the purity may further result in a decrease in side effects associated with low purity pharmaceutical formulations, an improvement in the measured half life of the drug formulation, and an improvement in drug targeting.

Representative Synthesis of High-Purity Samples or Compositions

Figure 1:
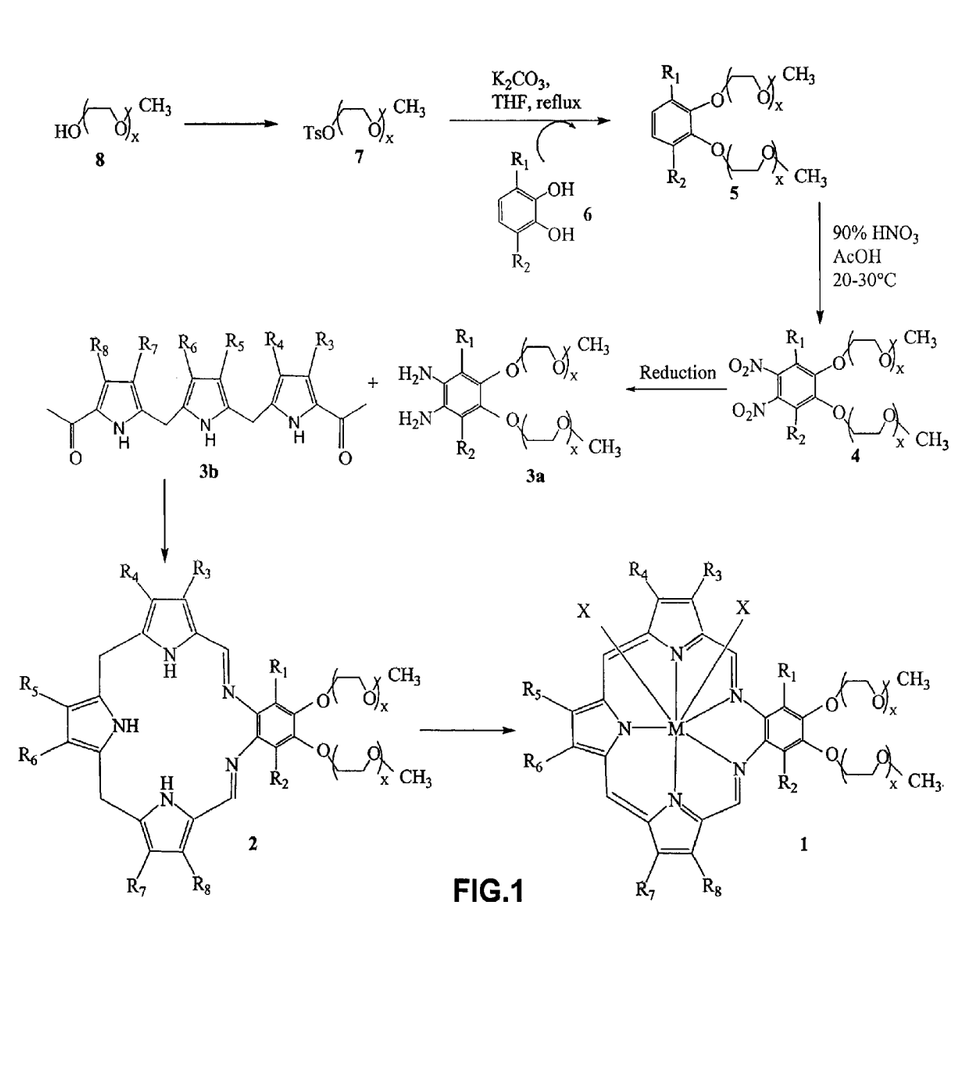
FIG. 1 schematically summarizes an illustrative synthesis of texaphyrin metal complexes described herein.

Without limiting the scope of the compositions and methods described herein, a representative synthesis of texaphyrin metal complexes is depicted in FIG. 1. A compound of Formula 8 (each x is 3) is tosylated to a compound of Formula 7. The tosylated compound of Formula 7 is treated with a o-dihydroxybenzene derivative of Formula 6 in the presence of $K_2CO_3$ and an aprotic solvent to result in a compound of Formula 5. The aprotic solvent, by way of example only, may be selected from the group consisting of aldehydes, ketones, dimethyl sulfoxide, dimethyl formamide, pyridine, diethyl ether, ethyl acetate, propyl acetate, isopropyl acetate, butyl acetate, acetonitrile, benzonitrile, sulfur dioxide, tetrahydrofuran, hexamethyl phophoramide, and the like. In one embodiment disclosed herein, the solvent is tetrahydrofuran.

The compound of Formula 5 is nitrated in the presence of nitric acid and acetic acid to result in a compound of Formula 4. A high purity sample of a compound having the structure of Formula 4 is thus obtained, wherein at least about 98.4% of the compounds of Formula 4 in the high purity sample have the same structure (and the same molecular weight, excluding isotopic variation), i.e. both polyethylene glycol chain lengths on the aromatic moiety have the same chain length.

In some embodiments disclosed herein, at least about 98.7%, 99%, 99.3% or 99.5% of the compounds of Formula 4 in the high purity sample have the same structure (and the same molecular weight, excluding isotopic variation), i.e.

both polyethylene glycol chain lengths on the aromatic moiety have the same chain length (including the same "x" value per the generic formula).

Figure 2:
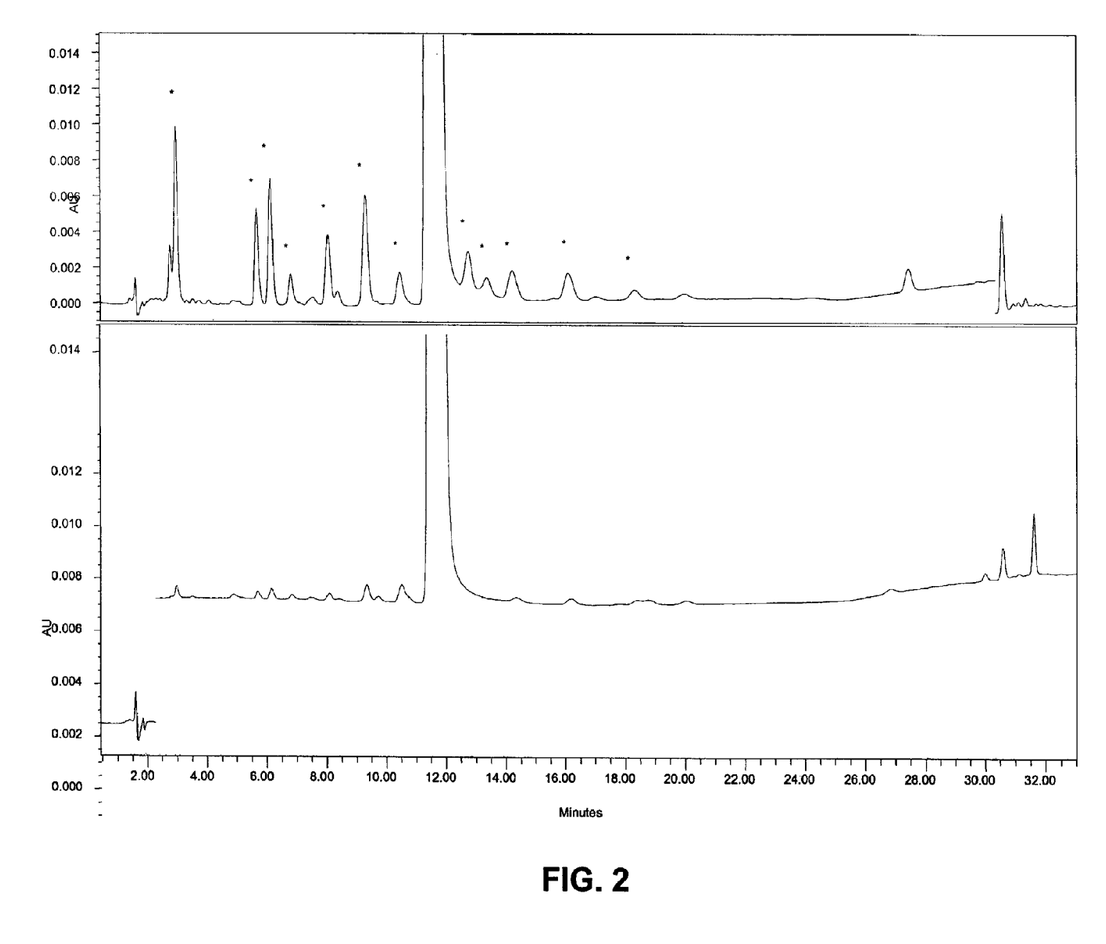
FIG. 2 shows an illustrative chromatogram comparing the purity of a compound of Formula 4 as synthesized by the old process and the improved process disclosed herein.

Table 1 compares the purity of compositions comprising compounds of Formula 4 made via the old process and the process disclosed herein. FIG. 2 is a chromatogram comparison of the purity of compositions comprising compounds of Formula 4 made via the old process and the process disclosed herein.

TABLE 1

Purity of compositions comprising compounds of Formula 4

| Batch Number | Purity | PEG impurities |
|---|---|---|
| Old Process | | |
| Batch 1 | 97.8% | 1.96% |
| Batch 2 | 98.2% | 1.61% |
| Batch 3 | 98.2% | 1.63% |
| Batch 4 | 97.7% | 2.01% |
| New Process | | |
| Batch 1 | 99.6% | 0.23% |
| Batch 2 | 99.6% | 0.21% |
| Batch 3 | 99.4% | 0.28% |
| Batch 4 | 99.4% | 0.24% |

The higher purity of the compounds may be attributable to a solvent used in the formation of the compound of Formula 5. During development of the compound of Formula 4, one particular impurity was identified as having a structure shown below:

This impurity was found in greater quantity than would be expected based on an amount of ethylene glycol monomethyl ether contained in compound of Formula 8. Without limiting the scope of the compositions and methods described herein, it is postulated that this impurity originates in the reaction step of the synthesis of compound of Formula 5 from compound of Formula 7 via an intermediate A shown below:

The 1,4-dioxane type molecule A is formed by an intramolecular attack of an ether oxygen to displace tosylate. The o-dihydroxybenzene derivative of Formula 6 can react with A to form either compound of Formula 5 or the monoethylene glycol/triethylene glycol impurity (mono/tri) as shown:

Without limiting the scope of the compositions and methods described herein, it is postulated that the 1,4-dioxane cation A might be stabilized in the ethanol solvent used in the old process. In methods disclosed herein, THF minimizes the formation of the mono/tri impurity. Table 2 depicts the % of mono/tri impurity obtained in different solvents. Ethanol results in 0.43% of mono/tri impurity whereas THF gives only 0.08% of mono/tri impurity.

TABLE 2

Comparison of Mono/tri impurity in different solvents

| | Compound of Formula 5 | | Compound of Formula 4 (solids) | | |
|---|---|---|---|---|---|
| Solvent | Temperature | Conv. Time (hr) | % Compound of Formula 4 | % mono/tri impurity | Yield (from o-dihydroxy benzene) |
| Ethanol | 78° C. | 6 | 99 | 0.43 | 68% |
| Ethanol | 50° C. | >48 | n/a | n/a | n/a |
| Acetonitrile | 80° C. | 8 | 98.6 | 0.41 | 79% |
| MTBE | 58-60° C. | 15 | 93 | 4.6 | ~50% |
| Propyl acetate | 90° C. | 2 | 97.9 | 0.13 | 66% |
| THF | 70° C. | 4 | 99.2 | 0.08 | 47% |

The compound of Formula 4 after reduction results in a phenylenediamine of Formula 3a which on condensation with a compound of Formula 3b results in a high purity sample, wherein at least about 98.4% of the compounds having a structure of Formula 2 in the high purity sample have the same structure (and the same molecular weight, excluding isotopic variation), i.e. both polyethylene glycol chain lengths on the aromatic moiety have the same chain length. In some embodiments disclosed herein, at least about 98.7%, 99%, 99.3% or 99.5% of the compounds of Formula 2 in the high purity sample have the same structure (and the same molecular weight, excluding isotopic variation), i.e. both polyethylene glycol chain lengths on the aromatic moiety have the same chain length (including the same "x" value per the generic formula).

Figure 3:
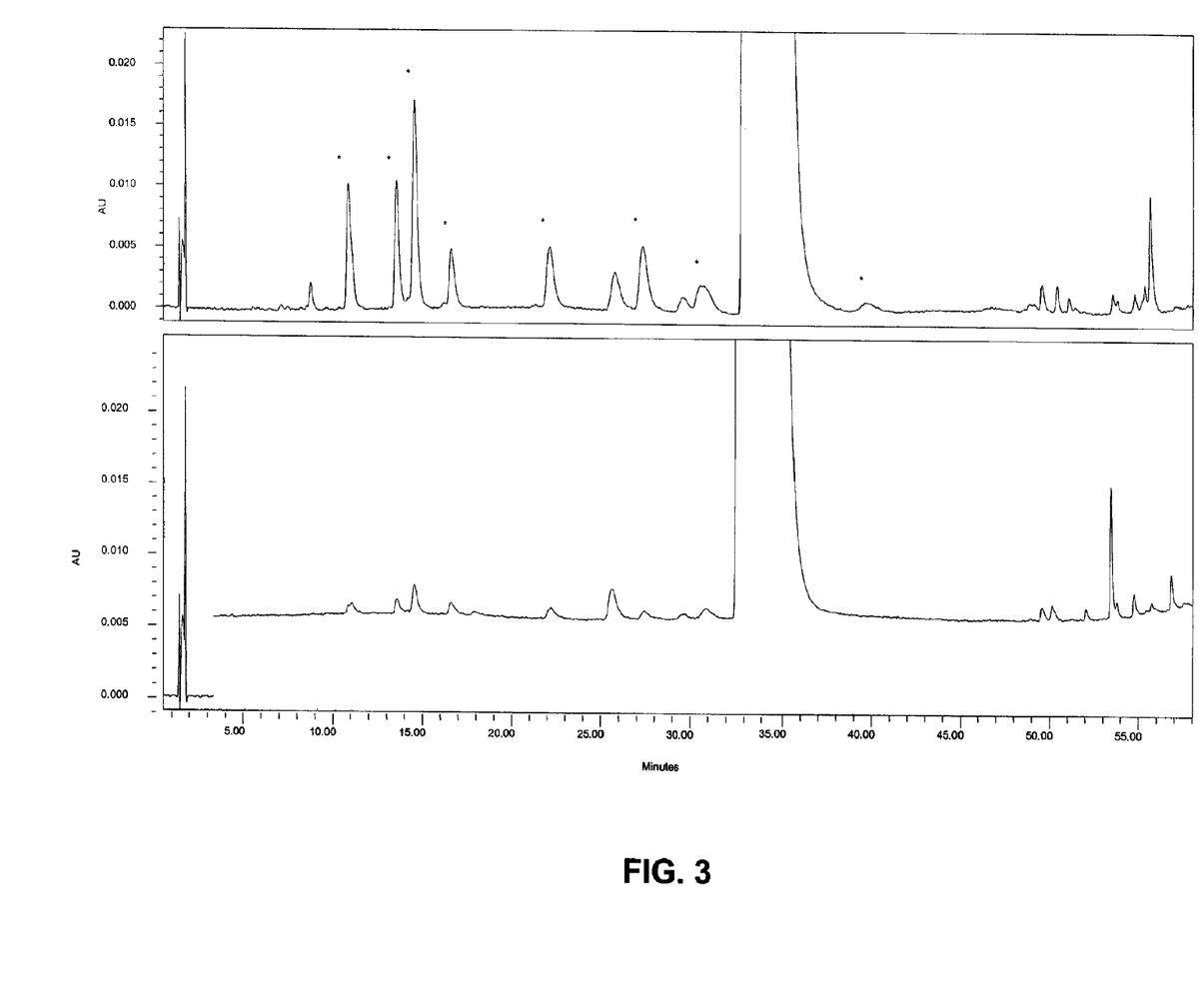
FIG. 3 shows an illustrative chromatogram comparing the purity of a compound of Formula 1 as synthesized by the old process and the improved process disclosed herein.

The compound of Formula 2 complexes oxidatively with a trivalent metal cation (M) to result in a high purity sample, wherein at least about 98.4% of the compounds having a structure of Formula 1 in the high purity sample have the same structure (and the same molecular weight, excluding isotopic variation), i.e. both polyethylene glycol chain lengths on the aromatic moiety have the same chain length. In some embodiments disclosed herein, at least about 98.7%, 99%, 99.3% or 99.5% of the compounds of Formula 1 in the high purity sample have the same structure (and the same molecular weight, excluding isotopic variation), i.e. both polyethylene glycol chain lengths on the aromatic moiety have the same chain length (including the same "x" value per the generic formula). Suitable M include, by way of example only, $Mn^{+3}$, $Co^{+3}$, $Ni^{+3}$, $Y^{+3}$, $In^{+3}$, $Pr^{+3}$, $Nd^{+3}$, $Sm^{+3}$, $Eu^{+3}$, $Gd^{+3}$, $Tb^{+3}$, $Dy^{+3}$, $Er^{+3}$, $Fe^{+3}$, $Ho^{+3}$, $Ce^{+3}$, $Tm^{+3}$, $Yb^{+3}$, $Lu^{+3}$, $Lu^{+3}$, and $U^{+3}$; further examples of M include divalent metal cations, such as $Mn^{+2}$, $Co^{+2}$, $Ni^{+2}$, and $Fe^{+2}$. In some embodiments disclosed herein, the trivalent metal ions are $Gd^{+3}$ or $Lu^{+3}$. Table 3 compares the purities of samples of compounds of Formula 1 made by the old process and in the process disclosed herein. The old process resulted in 96.6% purity whereas the process disclosed herein improves it to at least about 98.4%. FIG. 3 is a chromatogram comparison of the purity of compositions comprising compounds of Formula 1 made via the old process and the process disclosed herein.

TABLE 3

Purity of compositions comprising compounds of Formula 1

| Batch Number | Purity | PEG impurities |
|---|---|---|
| Old Process | | |
| Batch 1 | 96.0% | 2.45% |
| Batch 2 | 95.7% | 2.66% |
| Batch 3 | 96.5% | 2.44% |
| Batch 4 | 96.6% | 2.32% |
| Batch 5 | 95.2% | 2.74% |
| New Process | | |
| Batch 1 | 99.3% | 0.33% |
| Batch 2 | 99.1% | 0.38% |
| Batch 3 | 99.2% | 0.33% |
| Batch 4 | 99.2% | 0.25% |
| Batch 5 | 99.0% | 0.30% |

In the condensation step between compound 3a and 3b, the introduction of various substituents on the tripyrrole portion of the molecule may be accomplished by appropriate substitutions in the 3 and/or 4 positions of the pyrrole rings at a synthetic step prior to condensation with the substituted phenylenediamine. The substituents on the benzene ring may be obtained by appropriate substitutions in the benzene ring prior to condensation with the pyrrole rings.

Illustrative Methods for Determining Purity of a Sample or Composition

Without limiting the scope of the compositions and methods disclosed herein, some of the methods for demonstrating a purity of a compound are described.

Chromatographic methods that are contemplated to be used for demonstrating purity are, by way of example only, molecular size exclusion chromatography, native gel electrophoresis, high pressure liquid chromatography (HPLC), liquid chromatography (LC), liquid chromatography coupled with mass spectroscopy (LC/MS), gas chromatography (GC), GC coupled with mass spectroscopy (GC MS), supercritical fluid chromatography, gel permeation chromatography and ion exchange chromatography, and Reversed-Phase High Performance Liquid Chromatography.

Other methods that are contemplated to be used for demonstrating purity are, by way of example only, end group analysis, vapor pressure osmometry, cryoscopy/ebulliometry (freezing point depression/boiling point elevation), viscometry, small-angle X ray scattering, laser light scattering, optical absorption and scattering, ultracentrifugation, field flow fractionation, matrix-assisted laser desorption/ionization time-of-flight (MALDI-TOF) mass spectrometry, nuclear magnetic resonance spectrometry and crystallization.

Method for Treating Cancer

Without limiting the scope of the compositions and the methods disclosed herein, the methods are used to treat several specific cancers or tumors. Cancer types include (some of which may overlap in scope), by way of example only, adrenal cortical cancer, anal cancer, aplastic anemia, bile duct cancer, bladder cancer, bone cancer, bone metastasis, adult CNS brain tumors, pediatric CNS brain metastases, brain metastases, breast cancer, Castleman Disease, cervical cancer, childhood Non-Hodgkin's lymphoma, colon and rectum cancer, endometrial cancer, esophagus cancer, Ewing's family of tumors, eye cancer, gallbladder cancer, gastrointestinal carcinoid tumors, gastrointestinal stromal tumors, gestational trophoblastic disease, hematological malignancies, Hodgkin's disease, Kaposi'sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, nonmelanoma skin cancer, stomach cancer, testicular cancer, thymus cancer, thyroid cancer, uterine sarcoma, vaginal cancer, vulvar cancer, and Waldenstrom's macroglobulinemia. In one embodiment, the cancers are selected from the group consisting of metastatic brain cancer, lung cancer, glioblastoma, lymphomas, leukemia, renal cell cancer (kidney cancer), head and neck cancer, breast cancer, prostrate cancer, and ovarian cancer.

Disclosed herein are methods and compositions to treat lung cancer comprising administration of the high-purity compositions of Formula 1. Treatment options for lung cancer include (which can be provided to a patient in conjunction with administration of the high-purity compositions of Formula 1), by way of example only, surgery, immunotherapy, radiation therapy, chemotherapy, photodynamic therapy, or a combination thereof Some possible surgical options for treatment of lung cancer are a segmental or wedge resection, a lobectomy, or a pneumonectomy. Radiation therapy may be external beam radiation therapy or brachytherapy.

Disclosed herein are methods and compositions to treat CNS neoplasms comprising administration of the high-purity compositions of Formula 1. Treatment options for CNS neoplasms include (which can be provided to a patient in conjunction with administration of the high-purity compositions of Formula 1), by way of example only, surgery, radiation therapy, immunotherapy, hyperthermia, gene therapy, chemotherapy, and combination of radiation and chemotherapy. Doctors also may prescribe steroids to reduce the swelling inside the CNS.

Disclosed herein are methods to treat kidney cancer comprising administration of the high-purity compositions of Formula 1. Kidney cancer (also called renal cell cancer or renal adenocarcinoma) is a disease in which malignant cells are found in the lining of tubules in the kidney. Treatment options for kidney cancer include (which can be provided to a patient in conjunction with administration of the high-purity compositions of Formula 1), by way of example only, surgery, radiation therapy, chemotherapy and immunotherapy. Some possible surgical options to treat kidney cancer include, by way of example only, partial nephrectomy, simple nephrectomy and radical nephrectomy. Radiation therapy may be external beam radiation therapy or brachytherapy. Stem cell transplant may be used to treat kidney cancer.

In one embodiment disclosed herein are methods to treat lymphoma comprising administration of the high-purity compositions of Formula 1. Treatment options for lymphoma include (which can be provided to a patient in conjunction with administration of the high-purity compositions of Formula 1), by way of example only, chemotherapy, immunotherapy, radiation therapy and high-dose chemotherapy with stem cell transplant. Radiation therapy may be external beam radiation therapy or brachytherapy.

Disclosed herein are methods for treating breast cancer comprising administration of the high-purity compositions of Formula 1. Treatment options for breast cancer include (which can be provided to a patient in conjunction with administration of the high-purity compositions of Formula 1), by way of example only, surgery, immunotherapy, radiation therapy, chemotherapy, endocrine therapy, or a combination thereof. A lumpectomy and a mastectomy are two possible surgical procedures available for breast cancer patients.

Disclosed herein are methods for treating ovarian cancer, comprising administration of the high-purity compositions of Formula 1. Treatment options for ovarian cancer include (which can be provided to a patient in conjunction with administration of the high-purity compositions of Formula 1), by way of example only, surgery, immunotherapy, chemotherapy, hormone therapy, radiation therapy, or combinations thereof. Some possible surgical procedures include debulking, and a unilateral or bilateral oophorectomy and/or a unilateral or bilateral salpigectomy.

Disclosed herein are methods for treating cervical cancer, comprising administration of the high-purity compositions of Formula 1. Treatment options for cervical cancer include (which can be provided to a patient in conjunction with administration of the high-purity compositions of Formula 1), by way of example only, surgery, immunotherapy, radiation therapy and chemotherapy. Some possible surgical options are cryosurgery, a hysterectomy, and a radical hysterectomy. Radiation therapy for cervical cancer patients includes external beam radiation therapy or brachytherapy.

Disclosed herein are methods to treat prostate cancer, comprising administration of the high-purity compositions of Formula 1. Treatment options for prostate cancer include (which can be provided to a patient in conjunction with administration of the high-purity compositions of Formula 1), by way of example only, surgery, immunotherapy, radiation therapy, cryosurgery, hormone therapy, and chemotherapy. Possible surgical procedures to treat prostate cancer include, by way of example only, radical retropubic prostatectomy, a radical perineal prostatectomy, and a laparoscopic radical prostatectomy. Some radiation therapy options are external beam radiation, including three dimensional conformal radiation therapy, intensity modulated radiation therapy, and conformal proton beam radiation therapy. Brachytherapy (seed implantation or interstitial radiation therapy) is also an available method of treatment for prostate cancer. Cryosurgery is another possible method used to treat localized prostate cancer cells. Hormone therapy, also called androgen deprivation therapy or androgen suppression therapy, may be used to treat prostate cancer. Several methods of this therapy are available including an orchiectomy in which the testicles, where 90% of androgens are produced, are removed. Another method is the administration of luteinizing hormone-releasing hormone (LHRH) analogs to lower androgen levels. The LHRH analogs available include leuprolide, nafarelin, goserelin, triptorelin, and histrelin. An LHRH antagonist may also be administered, such as abarelix. Treatment with an antiandrogen agent, which blocks androgen activity in the body, is another available therapy. Such agents include flutamide, bicalutamide, and nilutamide. This therapy is typically combined with LHRH analog administration or an orchiectomy, which is termed a combined androgen blockade (CAB). Chemotherapy may be appropriate where a prostate tumor has spread outside the prostate gland and hormone treatment is not effective. Anti-cancer drugs may be administered to slow the growth of prostate cancer, reduce symptoms and improve the quality of life.

Disclosed herein are methods for treating leukemia, comprising administration of the high-purity compositions of Formula 1. Treatment options for leukemia include (which can be provided to a patient in conjunction with administration of the high-purity compositions of Formula 1), by way of example only, immunotherapy, radiation therapy, chemotherapy, bone marrow or peripheral blood stem cell transplantation, or a combination thereof. Radiation therapy includes external beam radiation and may have side effects. Anti-cancer drugs may be used in chemotherapy to treat leukemia. Monoclonal antibody therapy may be used to treat AML patients. Small molecules or radioactive chemicals may be attached to these antibodies before administration to a patient in order to provide a means of killing leukemia cells in the body. The monoclonal antibody, gemtuzumab ozogamicin, which binds CD33 on AML cells, may be used to treat AML patients unable to tolerate prior chemotherapy regimens. Bone marrow or peripheral blood stem cell transplantation may be used to treat AML patients. Some possible transplantation procedures are an allogenic or an autologous transplant.

Disclosed herein are methods and compositions to treat head and neck cancer, comprising administration of the high-purity compositions of Formula 1. Treatment options for head and neck cancer include (which can be provided to a patient in conjunction with administration of the high-purity compositions of Formula 1), by way of example only, surgery, radiation, chemotherapy, combined modality therapy, gene therapy, either alone or in combination thereof.

Method for Treating Cardiovascular Disease

Disclosed herein are the methods to treat cardiovascular diseases. Cardiovascular disease has two main components: Diseases of the heart (cardio) and Diseases of the blood vessels (vascular).

Coronary Artery Disease

These are diseases of the arteries that supply the heart muscle with blood. Sometimes known as CAD, coronary artery disease is the most common form of heart disease in industrialized nations and far and away the leading cause of heart attacks. Coronary artery disease generally means that blood flow through the arteries has become impaired. The most common way such obstructions develop is through a condition called atherosclerosis, a largely preventable type of vascular disease. These arteries, whose inner lining is normally smooth, can slowly become clogged with clumps of fats, cholesterol and other material, called atherosclerotic plaques. As a result, the supply of blood—with its oxygen and nutrients—going to the heart muscle is choked off (myocardial ischemia). Chest pain (angina pectoris) occurs, for instance, when the oxygen demand of the heart muscle exceeds the oxygen supply because of that narrowing in the coronary arteries. When the imbalance of oxygen supply lasts for more than a few minutes, heart muscle can begin to die, causing a heart attack (myocardial infarction). This may occur without symptoms (silent heart attack), especially in people with diabetes. In addition, the lack of blood, even briefly, can lead to serious disorders of the heart rhythm, known as arrhythmias or dysrhythmias. Coronary artery disease can even cause sudden death from an arrhythmia without any prior warning. A heart attack, for instance, can lead to congestive heart failure, and both of these conditions are types of cardiovascular disease. Other cardiovascular diseases are, by way of example only, cardiomyopathy, valvular heart disease, pericardial disease, congenital heart disease, and congestive heart failure.

Diseases of the blood vessels include, by way of example only, high blood pressure, aneurysms, occlusive artery disease, vasculitis, venus thrombosis.

Peripheral Artery Disease (PAD)

In PAD, fatty deposits build up in the inner linings of the artery walls. These blockages restrict blood circulation, mainly in arteries leading to the kidneys, stomach, arms, legs and feet. In its early stages a common symptom is cramping or fatigue in the legs and buttocks during activity. Such cramping subsides when the person stands still. This is called "intermittent claudication." People with PAD often have fatty buildup in the arteries of the heart and brain. Because of this association, people with PAD have a higher risk of death from heart attack and stroke. Treatments include, by way of example only, medicines to help improve walking distance, antiplatelet agents, and cholesterol-lowering agents (statins). Angioplasty or surgery may be necessary.

Saphenous Vein Graft Disease

This term refers to the narrowing, either localized or diffuse, of the segment of the saphenous vein that has been used as a bypass graft. Serial follow-up studies of patients who have undergone bypass surgery have shown that up to 10 percent of vein grafts are occluded by the time of hospital discharge, which increases to 20 percent by the end of the first year after surgery. With time, there is continued development of disease and progression, so that by the end of 10 years only one-third of the vein grafts that were not occluded at one year are free of significant disease. A re-operation becomes necessary in about 20 percent of patients by 10 years. Treatments include, by way of example only, medical therapy, surgery, and angioplasty.

The methods disclosed herein can provide a beneficial effect for patients suffering from aforementioned diseases, by administration of a compound of Formula 1 or a combination of administration of a compound of Formula 1 and at least one treatment identified in the foregoing paragraphs, including, by way of example only: surgery, radiation therapy, chemotherapy, transplantation therapy or the like. The choice of therapy that can be co-administered with the compositions disclosed herein will depend, in part, on the condition being treated. For example, for treating cancer, a compound of Formula 1 can be used in combination with radiation therapy, monoclonal antibody therapy, chemotherapy, bone marrow transplantation, gene therapy, immunotherapy, or a combination thereof. As another example, for treating CAD or PAD, a compound of Formula 1 can be used in combination with surgery, radiation therapy, chemotherapy, or transplantation therapy.

Formulations, Routes of Administration, and Effective Doses

Another aspect disclosed herein relates to pharmaceutical compositions comprising a compound of Formula 1 and a pharmaceutically acceptable excipient. Such pharmaceutical compositions can be used to treat cancer or cardiovascular disease in the methods as described herein.

The compounds of Formula 1 may be provided as a prodrug and/or may be allowed to interconvert to compound of Formula 1 in vivo after administration. The compounds of Formula 1 and/or its prodrug, or its pharmaceutically acceptable salts may be used in developing a formulation for use in the methods disclosed herein. Further, in some embodiments, the compound may be used in combination with one or more other compounds or in one or more other forms. The compound of Formula 1 may be formulated, in the same dosage unit e.g. in one cream, intravenously-suitable formulation, solution, suppository, tablet, or capsule.

The term "pharmaceutically acceptable salt" means those salts which retain the biological effectiveness and properties of the compounds disclosed herein, and which are not biologically or otherwise undesirable. For example, a pharmaceutically acceptable salt does not interfere with the beneficial effect of the compound disclosed herein in treating a cancer.

Typical salts include by way of example only, salts formed by mixing a compound of Formula 1 in an appropriate buffer, such as phosphate buffer, or by passing a compound of Formula 1 through an appropriate ion-exchange column. In addition, if the compounds disclosed herein contain a carboxy group or other acidic group, it may be converted into a pharmaceutically acceptable addition salt with inorganic or organic bases. Examples of suitable bases include by way of example only, sodium hydroxide, potassium hydroxide, ammonia, tromethamine, meglumine, cyclohexylamine, dicyclohexyl-amine, ethanolamine, diethanolamine and triethanolamine.

The high-purity compositions of Formula 1 may be administered in either single or multiple doses by any of the accepted modes of administration of agents having similar utilities, for example as described in those patents and patent applications incorporated by reference above, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, including, by way of example, by injection. The forms in which the high-purity compositions of Formula 1 may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the high-purity compositions of Formula 1 in the required amount in the appropriate solvent with various other ingredients as enumerated above, as required, followed by sterile filtration. Generally, dispersions are prepared by incorporating the various sterilized high-purity compositions of Formula 1 into a sterile vehicle which contains the basic dispersion medium and the required other ingredients from those enumerated above. In the case of sterile powders for the preparation of sterile injectable solutions, the methods of preparation are vacuum-drying and freeze-drying techniques, which yield a powder of the high-purity compositions of Formula 1 plus any additional desired ingredient from a previously sterile-filtered solution thereof.

The high-purity compositions of Formula 1 may be impregnated into a stent by diffusion, for example, or coated onto the stent such as in a gel form, for example, using procedures known to one of skill in the art in light of the present disclosure.

Oral administration is another route for administration of the high-purity compositions of Formula 1. Embodiments include oral administration via capsule or enteric-coated tablets, or the like, which prevent degradation of the high-purity compositions of Formula 1 in the stomach. In making the pharmaceutical compositions that include at least high-purity composition of Formula 1, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the high-purity compositions of Formula 1. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the high-purity compositions of Formula 1, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methylcellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The high-purity compositions of Formula 1 can be formulated so as to provide quick, sustained or delayed release of the high-purity compositions of Formula 1 after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods described herein employs transdermal delivery devices ("patches"). Such transdermal patches may be used to provide continuous or discontinuous infusion of the high-purity compositions of Formula 1 in controlled amounts, see, e.g., U.S. Pat. Nos. 5,023,252, 4,992,445 and 5,001,139. Such patches may be constructed for continuous, pulsatile, or on demand delivery of pharmaceutical agents.

The compositions are optionally formulated in a unit dosage form. The term "unit dosage form(s)" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The high-purity compositions of Formula 1 are effective over a wide dosage range and are generally administered in a pharmaceutically effective amount. For oral administration, each dosage unit contains from 10 mg to 2 g of a high-purity composition of Formula 1, and for parenteral administration, from 10 to 700 mg of a high-purity composition of Formula 1, including about 350 mg. The amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the high-purity composition of Formula 1 is mixed with a pharmaceutical excipient to form a solid preformulation composition containing a homogeneous mixture of a high-purity composition of Formula 1. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Such compositions are administered by the oral or nasal respiratory route for local or systemic effect. Compositions in pharmaceutically acceptable solvents may be nebulized by use of inert gases. Nebulized solutions may be inhaled directly from the nebulizing device or the nebulizing device may be attached to a facemask tent, or intermittent positive pressure-breathing machine. Solution, suspension, or powder compositions may be administered, orally or nasally, from devices that deliver the formulation in an appropriate manner.

The specific dose will vary depending on the particular high-purity composition of Formula 1 chosen, the dosing regimen to be followed, and the particular therapeutic energy or agent with which it is administered, employing dosages within the range of about 0.01 mg/kg per treatment up to about 100 mg/kg per treatment, preferably about 0.1 mg/kg per treatment to about 50 mg/kg per treatment. There are specific differences in the most effective dosimetry depending on the apical ligands chosen, because of the wide range of properties available, such as solubilities, lipophilicity properties, lower toxicity, and improved stability.

Administration for Photodynamic Therapy

By way of example, a high-purity composition of Formula 1, having lutetium as a metal in the texaphyrin, may be administered in solution, optionally in 5% mannitol USP. Dosages of about 1.0 to 2.0 mg/kg to about 4.0 to 7.0 mg/kg, including 3.0 mg/kg, are employed, although in some cases a maximum tolerated dose may be higher, for example about 5 mg/kg. The texaphyrin is administered by intravenous injection, followed by a waiting period of from as short a time as several minutes or about 3 hours to as long as about 72 or 96 hours (depending on the treatment being effected) to facilitate intracellular uptake and clearance from the plasma and extracellular matrix prior to the administration of photoirradiation.

Dose levels for certain uses may range from about 0.05 mg/kg to about 20 mg/kg administered in single or multiple doses (e.g., before each fraction of photoirradiation). The lower dosage range would be applicable, for example, to intra-arterial injection or for impregnated stents.

The optimum length of time between administration of high-purity compositions of Formula 1 and light treatment can vary depending on the mode of administration, the form of administration, and the type of target tissue. Typically, the high-purity compositions of Formula 1 persists for a period of minutes to hours, depending on the high-purity composition of Formula 1, the formulation, the dose, the infusion rate, as well as the type of tissue and tissue size.

When employing photodynamic therapy, a target area is treated with light, for example at about 740±16.5 nm. After the photosensitizing high-purity composition of Formula 1 has been administered, the tissue being treated is photo irradiated at a wavelength similar to the absorbance of the high-purity composition of Formula 1, usually either about 440 to 540 nm or about 700 to 800 nm, or about 450 to 520 nm, or about 720 to 780 nm, or about 460 to 500 nm or about 725 to 760 nm. The light source may be a laser, a light-emitting diode, or filtered light from, for example, a xenon lamp; and the light may be administered topically, endoscopically, or interstitially (via, e.g., a fiber optic probe), or intra-arterially. In one embodiment, the light is administered using a slit-lamp delivery system. The fluence and irradiance during the photo irradiating treatment can vary depending on the type of tissue, depth of target tissue, and the amount of overlying fluid or blood. For example, a total light energy of about 100 J/cm2 can be delivered at a power of 200 mW to 250 mW, depending upon the target tissue.

Administration with Chemotherapeutic Drugs

High-purity compositions of Formula 1 may be administered before, at the same time as, or after administration of one or more chemotherapeutic drugs. The high-purity composition of Formula 1 may be administered as a single dose, or it may be administered as two or more doses separated by an interval of time. The high-purity composition of Formula 1 may be administered concurrently with, or from about 1 minute to about 12 hours following administration of a chemotherapeutic drug, preferably from about 5 minutes to about 5 hours, more preferably about 4 to 5 hours. The dosing protocol may be repeated, from one to three times, for example. A time frame that has been successful in vivo is administration of a high-purity composition of Formula 1 about 5 minutes and about 5 hours after administration of a chemotherapeutic agent, with the protocol being performed once per week for three weeks. Administration may be intra-arterial injection, intravenous, intraperitoneal, intramuscular, subcutaneous, oral, topical, or via a device such as a stent.

Administering a high-purity composition of Formula 1 and a chemotherapeutic drug to the subject may be prior to, concurrent with, or following vascular intervention. The method may begin at a time roughly accompanying a vascular intervention, such as an angioplastic procedure, for example. Multiple or single treatments prior to, at the time of, or subsequent to the procedure may be used. "Roughly accompanying a vascular intervention" refers to a time period within the ambit of the effects of the vascular intervention. Typically, an initial dose of a high-purity composition of Formula 1 and chemotherapeutic drug will be within 6 to 12 hours of the vascular intervention, preferably within 6 hours thereafter. Follow-up dosages may be made at weekly, biweekly, or monthly intervals. Design of particular protocols depends on the individual subject, the condition of the subject, the design of dosage levels, and the judgment of the attending practitioner.

Administration for Radiation Sensitization

High-purity compositions of Formula 1, where the metal is gadolinium, may be administered in a solution containing about 2 mM of the compound of Formula 1, optionally in 5% mannitol USP/water (sterile and non-pyrogenic solution); in a further or alternative composition, the solution contains about 2.2 mM of the compound of Formula 1 (in addition to other components described herein). Dosages of 0.1 mg/kg up to as high as about 29.0 mg/kg have been delivered, preferably about 3.0 to about 15.0 mg/kg (for volume of about 90 to 450 mL) may be employed, optionally with pre-medication using anti-emetics when dosing above about 6.0 mg/kg. The compound is administered via intravenous infusion over about a 5 to 10 minute period, followed by a waiting period of about 2 to 5 hours to facilitate intracellular uptake and clearance from the plasma and extracellular matrix prior to the administration of radiation.

When employing whole brain radiation therapy, a course of 30 Gy in ten (10) fractions of radiation may be administered over consecutive days excluding weekends and holidays. In the treatment of brain metastases, whole brain megavolt radiation therapy is delivered with 60Co teletherapy or a $\geqq 4$ MV linear accelerator with isocenter distances of at least 80 cm, using isocentric techniques, opposed lateral fields and exclusion of the eyes. A minimum dose rate at the midplane in the brain on the central axis is about 0.5 Gy per minute.

High-purity compositions of Formula 1 used as radiation sensitizers may be administered before, or at the same time as, or after administration of the ionizing radiation. The high-purity composition of Formula 1 may be administered as a single dose, as an infusion, or it may be administered as two or more doses separated by an interval of time. Where the high-purity composition of Formula 1 is administered as two or more doses, the time interval between the high-purity composition of Formula 1 administrations may be from about one minute to a number of days, from about 5 minutes to about 1 day, or from about 10 minutes to about 10 hours. The dosing protocol may be repeated, from one to ten or more times, for example. Dose levels for radiation sensitization may range from about 0.05 mg/kg to about 20 mg/kg administered in single or multiple doses (e.g. before each fraction of radiation). The lower dosage range would be preferred for intra-arterial injection or for impregnated stents.

Administration may be intra-arterial injection, intravenous, intraperitoneal, intramuscular, subcutaneous, oral, topical, or via an impregnated or coated device such as a stent, for example, or an artery-inserted cylindrical polymer. In one aspect of the methods for treating described herein, a patient having restenosis or at risk for restenosis is administered a dose of high-purity composition of Formula 1 at intervals with each dose of photoirradiation.

Administering a high-purity composition of Formula 1 to the subject may be prior to, concurrent with, or following vascular intervention, and the intervention is followed by photoirradiation. The method may begin prior to, such as about 24 to 48 hours prior to, or at a time roughly accompanying vascular intervention, for example. Multiple or single treatments prior to, at the time of, or subsequent to the procedure may be used. "Roughly accompanying the vascular intervention" refers to a time period within the ambit of the effects of the vascular intervention. Typically, an initial dose of a high-purity composition of Formula 1 and light will be within 1 to 24 hours of the vascular intervention, preferably within about 5 to 24 hours thereafter. Follow-up dosages may be made at weekly, biweekly, monthly or longer intervals. Design of particular protocols depends on the individual subject, the condition of the subject, the design of dosage levels, and the judgment of the attending practitioner.

Administration for Sonodynamic Therapy

The use of texaphyrins in sonodynamic therapy is described in U.S. patent application Ser. No. 09/111,148, which was converted to U.S. Provisional Application Ser. No. 60/155,256, from which a continuation was filed on Jan. 5, 2001, having U.S. patent application Ser. No. 09/755,824, now abandoned, which is incorporated herein by reference. Texaphyrin is administered before administration of the ultrasound. The texaphyrin may be administered as a single dose, or it may be administered as two or more doses separated by an interval of time. Parenteral administration is typical, including by intravenous and interarterial injection. Other common routes of administration can also be employed.

Ultrasound is generated by a focused array transducer driven by a power amplifier. The transducer can vary in diameter and spherical curvature to allow for variation of the focus of the ultrasonic output. Commercially available therapeutic ultrasound devices may be employed in the practice of such a method. The duration and wave frequency, including the type of wave employed may vary, and the preferred duration of treatment will vary from case to case within the judgment of the treating physician. Both progressive wave mode patterns and standing wave patterns have been successful in producing cavitation of diseased tissue. When using progressive waves, the second harmonic can advantageously be superimposed onto the fundamental wave. Types of ultrasound employed in such a method are ultrasound of low intensity, non-thermal ultrasound, i.e., ultrasound generated within the wavelengths of about 0.1 MHz and 5.0 MHz and at intensities between about 3.0 and 5.0 W/cm2.

In further applications, the compound of Formula 1, where M is Gd+3, may be administered with NAD(P)H, ascorbate and other reducing agents under approximate physiological conditions, leading to reactive oxygen species generation. Depletion of these reducing agents will inhibit biochemical pathways that in vivo utilize reducing agents to effect repair of the damage inflicted by reactive oxygen species. Such a method may be used to treat cancer and cardiovascular diseases. See U.S. Pat. No. 6,825,186, which is incorporated by reference in its entirety. The ability of compositions comprising a compound of Formula 1 to catalyze the oxidation of these reducing agents is expected to improve as the purity of the composition improves; hence, the high-purity compositions described herein are expected to result in an improved catalytic, and therapeutic, effectiveness.

While embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

EXAMPLES

All solvents and reagents were of reagent grade quality, purchased commercially, and used as received.

Example 1

Synthesis of a Compound of Formula 7 (x=3)

A solution of compound of Formula 8 (x=3; 74 g) in tetrahydrofuran (39 g) was added to an aqueous solution of sodium hydroxide (25%, 235 g), maintaining the temperature at 0-10° C. (see FIG. 1). It is important to maintain the temperature within this range. A solution of p-toluenesulfonyl chloride (TsCl, 78 g) in tetrahydrofuran (126 g) was added to compound of Formula 8 over 4 hours, also at 0-10° C. The reaction mixture was stirred for up to 90 minutes and neutralized by an addition of dilute hydrochloric acid (33%, 115 g) at 0-10° C. The lower aqueous layer was discarded and the organic layer was washed twice with brine (24%, 55 ml). The resulting solution of compound of Formula 7 in tetrahydrofuran is used directly in the next step.

Example 2

Synthesis of a Compound of Formula 5 (x=3; R1=R2=H)

o-Dihydroxybenzene (25 g), potassium carbonate (61 g) and the solution of compound of Formula 7 (x=3) were mixed and heated at reflux until ≦0.5% compound of Formula 7 remained (24-28 hr) (see FIG. 1). The reaction mixture was filtered and the filter cake was washed twice with tetrahydrofuran (92 g). The combined filtrates were concentrated under reduced pressure and a temperature of up to 110° C. The residue was cooled and treated with aqueous sodium hydroxide solution (6.5%, 315 g) at 20-30° C. Dichloromethane (106 ml) was added and the mixture agitated and separated. The organic phase was washed with water (150 ml) and distilled to dryness at up to 100° C. at atmospheric pressure. The residue was dissolved in acetic acid (~60 g) and used as an acetic acid solution in the next step.

Example 3

Synthesis of a Compound of Formula 4 (x=3; R1=R2=H)

A solution of compound of Formula 5 (x=3; R1=R2=H) in acetic acid was added to 90% nitric acid (580 g) at a temperature of 0-5° C. The reaction was stirred for 30-60 minutes at this temperature, then quenched by addition to water (620 ml) at 0-10° C. The reaction mixture was extracted twice with dichloromethane (265 ml followed by 130 ml), and the combined organic phases was washed with aqueous sodium hydroxide solution (5%, about 360 kg) at pH 5.5-8.5 and then with water (350 ml). The dichloromethane was distilled under reduced pressure and was replaced by IPA (50 g), which was also distilled, leaving the crude compound of Formula 4 as oil at 50-60° C. The crude compound of Formula 4 was added slowly to IPA (600 g) at 2-6° C. (critical parameter) and the mixture was held at this temperature for at least 1 hr. The precipitated compound of Formula 4 was filtered and washed with cold IPA. The wet cake was melted at 50-60° C. and the crystallization procedure was repeated. The wet cake was then dried at 25° C. under reduced pressure. 1H NMR (CDCl3): δ 3.37 (6H, s, OCH3), 3.53-3.56 (4H, m, PEG group), 3.62-3.64 (4H, m, PEG group), 3.65-3.67 (4H, m, PEG group), 3.71-3.74 (4H, m, PEG group), 3.92 (4H, t, PEG group), 4.31 (4H, t, PEG group), 7.49 (2H, s, aromatic). 13C NMR (CDCl3): δ 58.93, 69.53, 70.01, 70.60, 70.69, 71.05, 71.94, 109.56, 136.73, 151.81. LC/MS (APCI mode), MH+: m/e 493.2. Elemental analysis: calcd. for C20H32N2O12: C, 48.78; H, 6.55; N, 5.69. Found: C, 48.77; H, 6.55; N, 5.54.

What is claimed is:

1. In a process for synthesizing a purified sample of a compound of Formula 1:

Formula 1 wherein:

M is $Gd^{3+}$ or $Lu^{3+}$;

each X is independently selected from the group consisting of $OH^-$, $AcO^-$, $Cl^-$, $Br^-$, $I^-$, $F^-$, $H_2PO_4^-$, $ClO^-$, $ClO_2^-$, $ClO_3^-$, $ClO_4^-$, $HCO_3^-$, $HSO_4^-$, $NO_3^-$, $N_3^-$, $CN^-$, $SCN^-$, and $OCN^-$;

$R_4$ and $R_7$ are $C_3H_6OH$;

$R_5$ and $R_6$ are $C_2H_5$;

$R_3$ and $R_8$ are $CH_3$;

$R_1$ and $R_2$ are H; and each x is independently selected from the group consisting of 1, 2, 3, 4, 5, and 6;

the improvement comprises synthesizing a purified sample of a compound of Formula 1 wherein each x is 3 in at least about 98.4% of compounds of Formula 1 in the purified sample;

the process comprising the steps of:
i. pegylating a compound of Formula 6 comprising reacting a compound of Formula 7

Formula 7 with an o-dihydroxybenzene of Formula 6:

Formula 6 in tetrahydrofuran to provide a compound of Formula 5 having the structure:

Formula 5

2. In a process for synthesizing a purified sample of a compound of Formula 1:

Formula 1 wherein:

M is $Gd^{3+}$ or $Lu^{3+}$;

each X is independently selected from the group consisting of $OH^-$, $AcO^-$, $Cl^-$, $Br^-$, $I^-$, $F^-$, $H_2PO_4^-$, $ClO^-$, $ClO_2^-$, $ClO_3^-$, $ClO_4^-$, $HCO_3^-$, $HSO_4^-$, $NO_3^-$, $N_3^-$, $CN^-$, $SCN^-$, and $OCN^-$;

$R_4$ and $R_7$ are $C_3H_6OH$;

$R_5$ and $R_6$ are $C_2H_5$;

$R_3$ and $R_8$ are $CH_3$;

$R_1$ and $R_2$ are H; and each x is independently selected from the group consisting of 1, 2, 3, 4, 5, and 6;

the improvement comprises synthesizing a purified sample of a compound of Formula 1 wherein each x is 3 in at least about 98.4% of compounds of Formula 1 in the purified sample;

the process comprising the steps of:

i. pegylating a compound of Formula 6 comprising reacting a compound of Formula 7

Formula 7 with an o-dihydroxybenzene of Formula 6:

Formula 6 in tetrahydrofuran to provide a compound of Formula 5 having the structure:

Formula 5 wherein the compound of Formula 5 is used directly in the next step without purification;

ii. nitration of the compound of Formula 5 to provide a compound of Formula 4 and having the structure:

Formula 4 iii. reduction of a compound of Formula 4 to provide a phenylenediamine of Formula 3a:

Formula 3a iv. condensation of a compound of Formula 3a with a compound of Formula 3b:

Formula 3b to provide a compound of Formula 2 and having the structure:

Formula 2 and v. complexation of a compound of Formula 2 with a metal cation to provide a compound of Formula 1.

3. The method of claim 2, wherein each X is $AcO^-$.

4. The method of claim 2, wherein each x is 3 in at least about 99.3% of the compounds of Formula 1 in the composition.

* * * * *